(12) United States Patent
Ishima

(10) Patent No.: US 10,830,979 B2
(45) Date of Patent: Nov. 10, 2020

(54) WEIGHT BALANCE METHOD OF SURGICAL MICROSCOPE AND MECHANISM THEREOF

(71) Applicant: MITAKA KOHKI CO., LTD., Tokyo (JP)

(72) Inventor: Minoru Ishima, Kanagawa (JP)

(73) Assignee: MITAKA KOHKI CO., LTD., Tokyo (JP)

(*) Notice: Subject to any disclaimer, the term of this patent is extended or adjusted under 35 U.S.C. 154(b) by 212 days.

(21) Appl. No.: 16/002,311

(22) Filed: Jun. 7, 2018

(65) Prior Publication Data
US 2019/0377149 A1  Dec. 12, 2019

(51) Int. Cl.
| | | |
|---|---|---|
| *G02B 21/00* | (2006.01) | |
| *G02B 7/00* | (2006.01) | |
| *A61B 50/26* | (2016.01) | |
| *A61B 90/25* | (2016.01) | |
| *F16M 11/06* | (2006.01) | |
| *F16M 11/18* | (2006.01) | |
| *A61B 90/50* | (2016.01) | |

(52) U.S. Cl.
CPC .............. *G02B 7/001* (2013.01); *A61B 50/26* (2016.02); *A61B 90/25* (2016.02); *A61B 90/50* (2016.02); *F16M 11/06* (2013.01); *F16M 11/18* (2013.01)

(58) Field of Classification Search
CPC ...... G02B 7/001; G02B 21/362; G02B 21/00; A61B 50/26; A61B 90/25; A61B 90/50; F16M 11/06; F16M 11/08; F16M 11/10; F16M 11/18
See application file for complete search history.

(56) References Cited

U.S. PATENT DOCUMENTS

| | | | | |
|---|---|---|---|---|
| 6,045,104 A * | 4/2000 | Nakamura | ............. | F16M 11/10 248/123.11 |
| 7,472,872 B2 * | 1/2009 | Nakamura | ........... | F16M 11/105 248/123.2 |
| 7,724,428 B2 * | 5/2010 | Nakamura | ......... | G02B 21/0012 359/384 |
| 8,416,492 B2 * | 4/2013 | Enge | ..................... | G02B 7/001 359/368 |
| 8,830,572 B2 * | 9/2014 | Graber | .................. | G02B 7/001 248/123.11 |
| 10,288,859 B2 * | 5/2019 | Nakamura | ............. | A61B 90/20 |

FOREIGN PATENT DOCUMENTS

JP  4504081  7/2010

* cited by examiner

*Primary Examiner* — Thong Q Nguyen
(74) *Attorney, Agent, or Firm* — Greenblum & Bernstein, P.L.C.

(57) ABSTRACT

A weight balance method of a surgical microscope is able to automatically align, in response to a switching operation, a center of gravity G of the surgical microscope 5 with a rotary shaft S. A weight balance of the surgical microscope is easily attained only by slanting the surgical microscope, and therefore, no part of the surgical microscope protrudes upward to interfere with a supporting structure of the surgical microscope.

3 Claims, 11 Drawing Sheets

WEIGHT BALANCE METHOD OF SURGICAL MICROSCOPE AND MECHANISM THEREOF

BACKGROUND OF THE INVENTION

1. Field of the Invention

The present invention relates to an automatic weight balance method of a surgical microscope and a mechanism for achieving the method.

2. Description of Related Art

A surgical microscope used for neurosurgery and the like is supported with a support arm of a stand apparatus. The surgical microscope is a stereoscopic microscope having on its front side a left-right pair of eyepieces and supported to be rotatable around a horizontal rotary shaft which is arranged at an attaching part of the support arm and extends in a left-right direction. Interposed between the surgical microscope and the rotary shaft is an electric slide mechanism that has a cross shape and is capable of sliding the surgical microscope in front-back and up-down directions relative to the rotary shaft.

The electric slide mechanism is to align the center of gravity of the surgical microscope with the rotary shaft to establish a weight balance of the surgical microscope around the rotary shaft. Once the weight balance is established, the surgical microscope can be turned to an optional rotational position by freeing the rotary shaft and can be stopped at a given rotational position without supporting the surgical microscope with the hand. In the weight balanced state, the surgical microscope can optionally be turned without resistance, and therefore, surgery can easily be carried out by changing the orientation of the surgical microscope. A related art is, for example, Japanese Patent Publication No. 4504081 (Patent Literature 1).

Aligning the center of gravity of the surgical microscope with the rotary shaft of the support arm requires two steps. First, the surgical microscope is set horizontal and a front-back weight balance around the rotary shaft is established by sliding the surgical microscope with the electric slide mechanism. Next, the surgical microscope is manually turned by 90 degrees into a vertical posture in which the front-back weight balance around the rotary shaft is reestablished by sliding the surgical microscope with the electric slide mechanism. These two steps of operation make the center of gravity of the surgical microscope completely agree with the rotary shaft. Then, the surgical microscope can be turned, without breaking the weight balanced state, to an optional angle around the rotary shaft that is freed. Even if the hand is removed from the surgical microscope, the surgical microscope is stationary at a given position without turning.

This related art, however, needs two steps of operation to adjust the center of gravity of the surgical microscope to the rotary shaft. This is bothersome. In addition, the second operation of turning the surgical microscope by 90 degrees into an upright posture upwardly swings an ancillary device attached to a rear part of the surgical microscope, and therefore, the ancillary device may interfere with a part of the support arm of the stand apparatus.

In consideration of such problems of the related art, the present invention provides an automatic weight balance method of a surgical microscope and a mechanism for achieving the method, capable of automatically adjusting, only by one action, the center of gravity of the surgical microscope to a rotary shaft without turning the surgical microscope by 90 degrees.

SUMMARY OF THE INVENTION

According to an aspect of the present invention, the automatic weight balance method is for a surgical microscope having on its front side a left-right pair of eyepieces and being attached through an electric slide mechanism, which is slidable in up-down and front-back directions of the surgical microscope, to an attaching part arranged at a front end of a support arm of a stand apparatus, the surgical microscope together with the electric slide mechanism being turned around a horizontal rotary shaft extending in a left-right direction by an electric driving unit having a clutch. The method includes starting, in response to a switching operation, the electric driving unit to turn the surgical microscope together with the electric slide mechanism around the rotary shaft to a horizontal state, once the surgical microscope is set to the horizontal state, making the rotary shaft freely turn and detecting a front-back weight balance of the surgical microscope including the electric slide mechanism, if the front-back weight balance is imbalanced, driving the electric slide mechanism to slide the surgical microscope in a balancing direction, if the front-back weight balance is balanced, driving the electric driving unit to turn the surgical microscope together with the electric slide mechanism around the rotary shaft to an oblique state, once the surgical microscope is set to the oblique state, making the rotary shaft freely turn and detecting a front-back weight balance of the surgical microscope including the electric slide mechanism, and if the front-back weight balance is imbalanced, driving the electric slide mechanism to slide the surgical microscope in a balancing direction along a direction of the oblique state so that a center of gravity of the surgical microscope including the electric slide mechanism agrees with the rotary shaft.

DESCRIPTION OF PREFERRED EMBODIMENT

Figure 3:
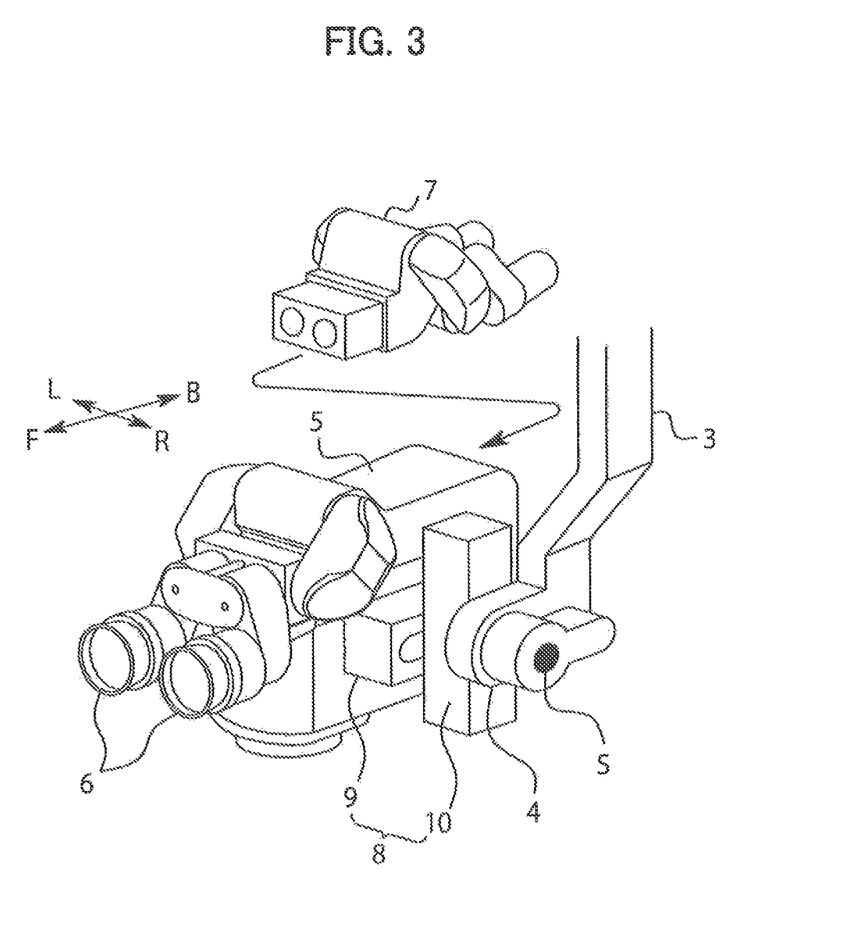
FIG. 3 is a perspective view illustrating the surgical microscope and a co-observation unit.

An embodiment of the present invention will be explained with reference to FIGS. 2 to 13. In this specification, a front direction (F) is an eyepiece 6 side of a surgical microscope 5, a back direction (B) is opposite to the front direction, and left (L) and right (R) directions are the left and right of the surgical microscope 5 seen from the eyepiece 6 side, as illustrated in FIG. 3.

Figure 2:
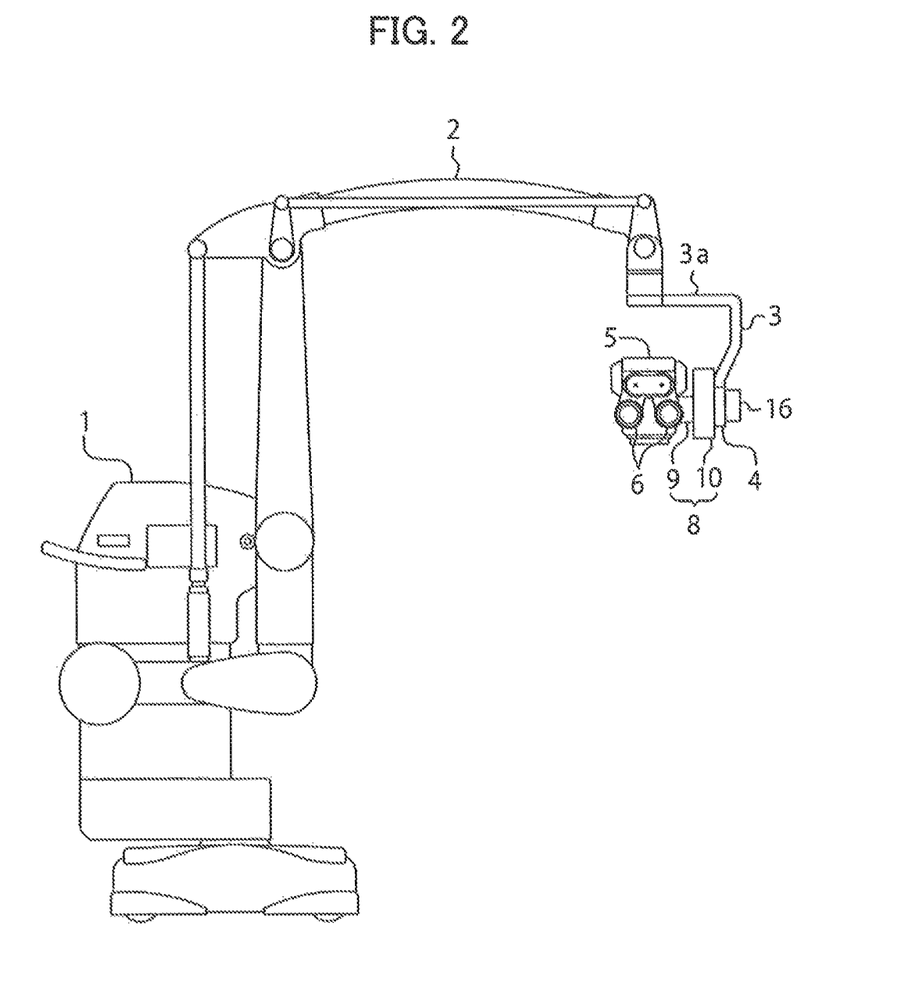
FIG. 2 is a side view illustrating a surgical microscope supported on a stand apparatus, according to an embodiment of the present invention.

First, a stand apparatus 1 will be explained. The stand apparatus 1 has a support arm 2 that is arranged at an upper part of the stand apparatus 1 and laterally extends. A front end of the support arm 2 has a suspension arm 3.

The suspension arm 3 is formed in an L-shape and has an upper horizontal part 3a. A lower end of the suspension arm 3 is an attaching part 4 to which the surgical microscope 5 is attached. The surgical microscope 5 is a stereoscopic microscope having on its front side a left-right pair of eyepieces (collectively referred to as the "eyepiece 6"). A back side of the surgical microscope 5 is provided with, if required, a co-observation unit 7.

Figure 5:
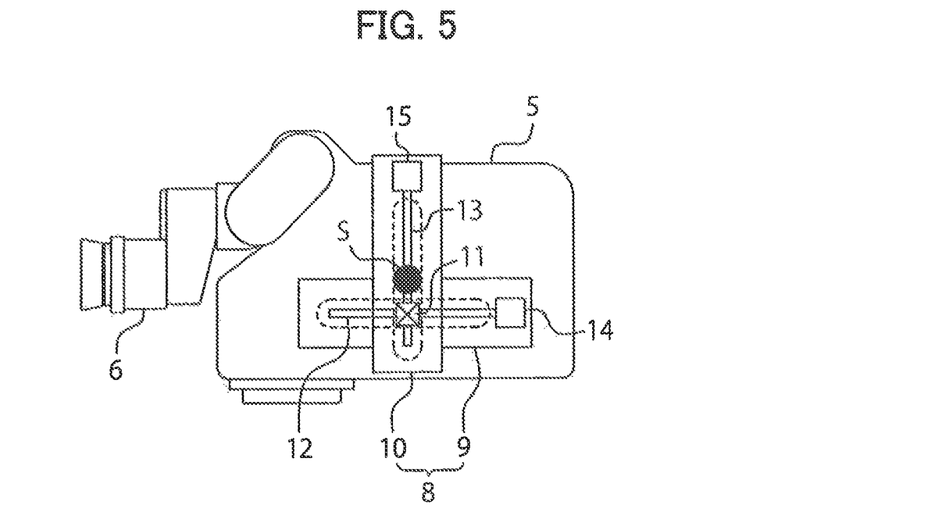
FIG. 5 is a side view illustrating an electric slide mechanism of the surgical microscope.
Figure 6:
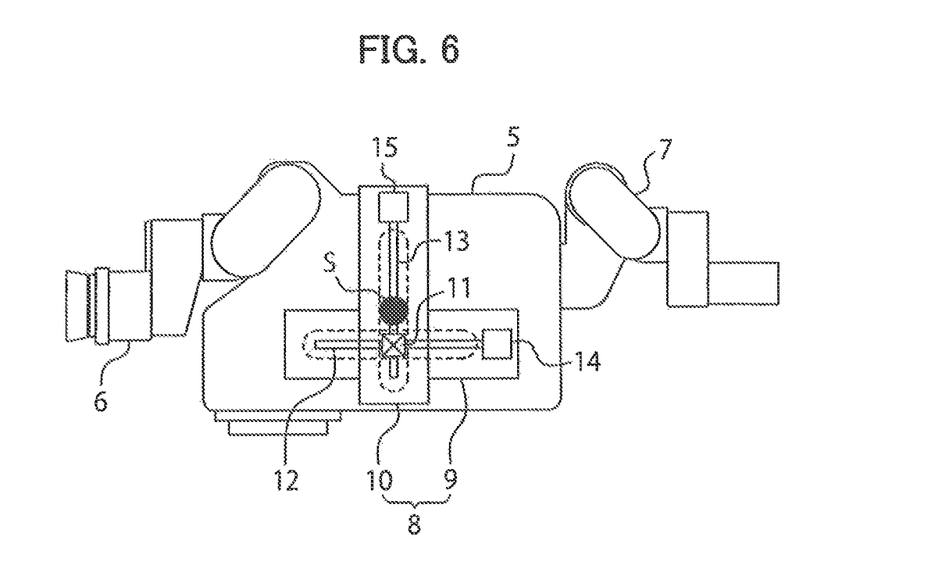
FIG. 6 is a side view corresponding to FIG. 5, illustrating the surgical microscope and the co-observation unit attached thereto.

A right side face of the surgical microscope 5 is attached through an electric slide mechanism 8 to the attaching part 4 of the suspension arm 3. The electric slide mechanism 8 includes a lateral slider 9 and a longitudinal slider 10. The lateral and longitudinal sliders 9 and 10 are connected to each other through a common connection member 11.

Figure 9:
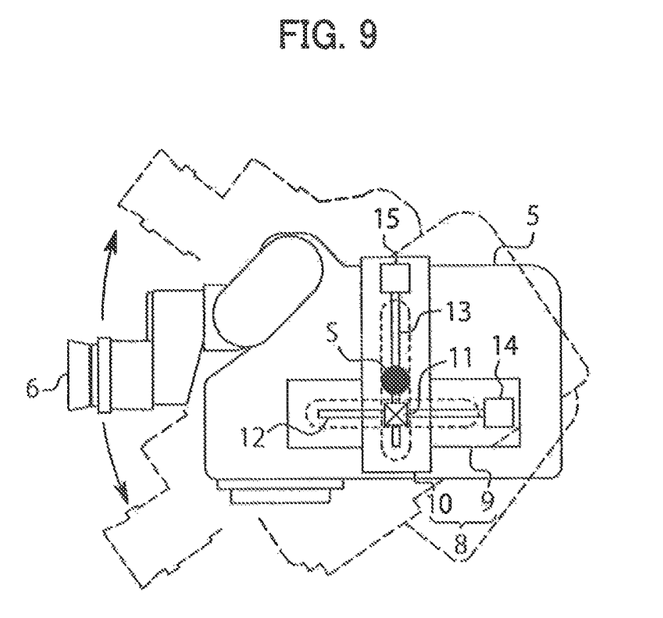
FIG. 9 is a view corresponding to FIG. 5, illustrating the surgical microscope turned around a rotary shaft.
Figure 10:
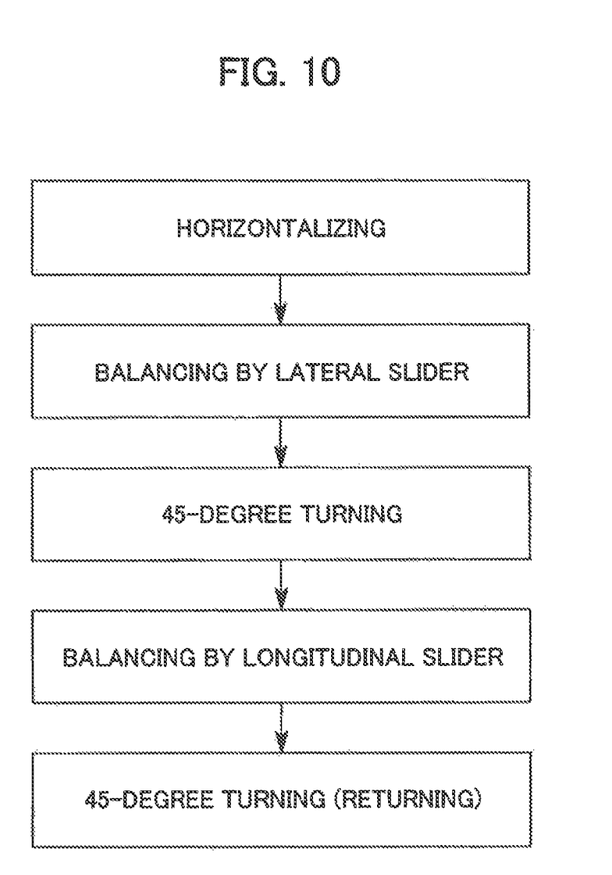
FIG. 10 is a flowchart illustrating steps of an automatic weight balancing method according to an embodiment of the present invention.

The lateral slider 9 is fixed to the right side face of the surgical microscope 5 and is extended in a front-back direction of the surgical microscope 5. The longitudinal slider 10 is extended in an up-down direction of the surgical microscope 5 and is attached to the attaching part 4 of the suspension arm 3. The longitudinal slider 10, however, is not completely fixed to the attaching part 4 but is rotatably attached thereto so that the longitudinal slider 10 may turn around a rotary shaft S arranged on the attaching part 4, as illustrated in FIG. 9. The rotary shaft S is a horizontal shaft extending in a left-right direction of the surgical microscope 5.

Figure 7:
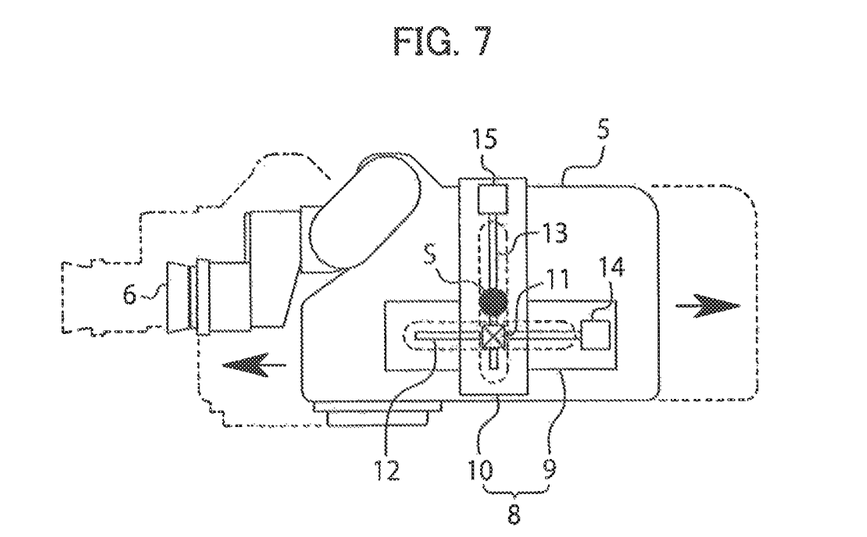
FIG. 7 is a view corresponding to FIG. 5, illustrating the surgical microscope slid in a front-back direction.
Figure 8:
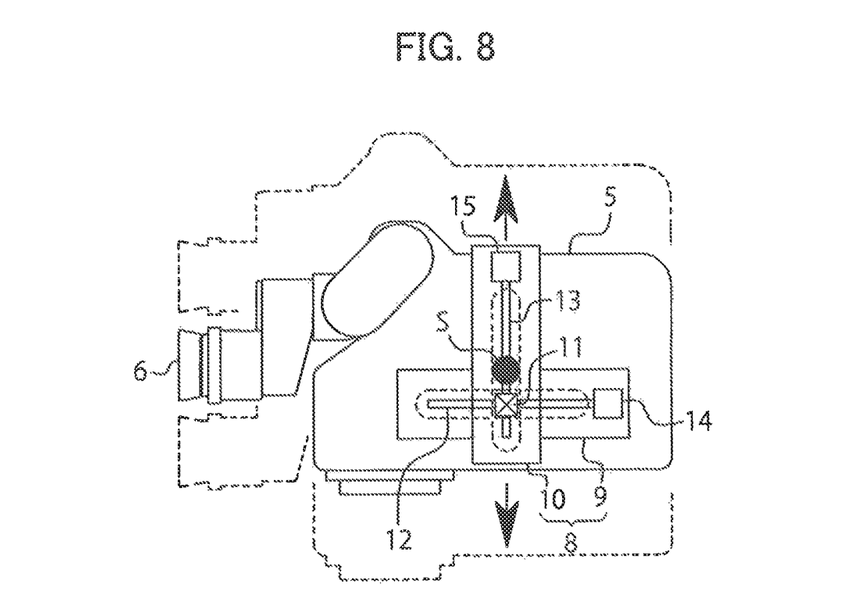
FIG. 8 is a view corresponding to FIG. 5, illustrating the surgical microscope slid in an up-down direction.

The common connection member 11 that connects the lateral and longitudinal sliders 9 and 10 to each other is threaded to pass screw rods 12 and 13, the screw rod 12 being arranged along the lateral slider 9 and the screw rod 13 along the longitudinal slider 10. The screw rods 12 and 13 are provided with electric motors 14 and 15, respectively, that drive the respective screw rods 12 and 13 in normal and reverse directions. Turning the screw rod 12 of the lateral slider 9 results in sliding the lateral slider 9 together with the surgical microscope 5 in the front-back direction relative to the longitudinal slider 10, as illustrated in FIG. 7. Turning the screw rod 13 of the longitudinal slider 10 results in sliding the lateral slider 9 together with the surgical microscope 5 in the up-down direction along the longitudinal slider 10, as illustrated in FIG. 8.

Figure 4:
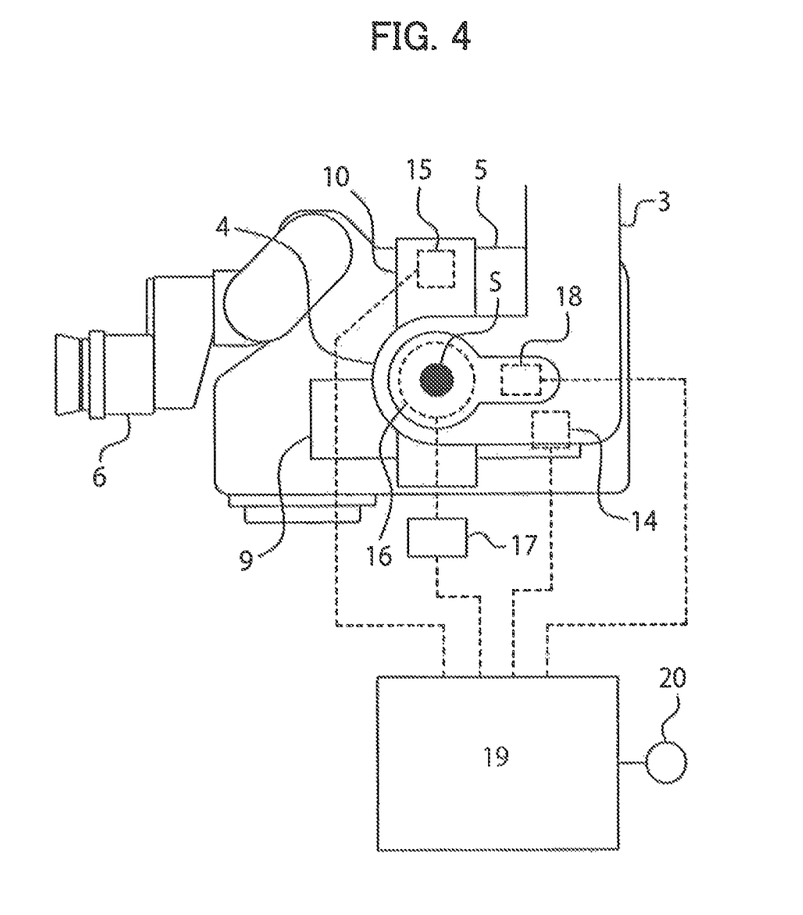
FIG. 4 is a view illustrating a control mechanism of the surgical microscope.

With reference to FIG. 4, a control mechanism of the surgical microscope 5 will be explained. The rotary shaft S arranged on the attaching part 4 is provided with an electric driving unit 16 having a clutch mechanism. With a driving force 5 of an electric motor, the electric driving unit 16 is able to turn the surgical microscope 5 together with the electric slide mechanism 8 in a required direction by a required amount. The clutch mechanism of the electric driving unit 16 is able to release the rotary shaft S to separate the surgical microscope 5 together with the electric slide mechanism 8 from the electric driving unit 16 so that the surgical microscope 5 may be manually and freely turned together with the electric slide mechanism 8. The rotary shaft S is provided with a horizontal sensor 17 to detect a horizontal state of the surgical microscope 5 and a balance sensor 18 to detect a weight balance of the surgical microscope 5 in the front-back direction around the rotary shaft S.

The electric motors 14 and 15 of the electric slide mechanism 8, the horizontal sensor 17, the electric driving unit 16, and the balance sensor 18 are electrically connected to a control unit 19. The control unit 19 is also connected to a switch 20 to start a balance adjustment.

Steps of automatically adjusting a weight balance of the surgical microscope 5 will be explained.

If the co-observation unit 7 is installed on the back side of the surgical microscope 5, a center of gravity G of the surgical microscope 5 as a whole will significantly come off the rotary shaft S. If the rotary shaft S is freed in this state, an imbalanced weight balance of the surgical microscope 5 around the rotary 30 shaft S causes the surgical microscope 5 to turn in one direction. The surgical microscope 5 in this state is unusable. To avoid this, the surgical microscope 5 must be adjusted before use such that the center of gravity G of the surgical microscope 5 is on the rotary shaft S.

To make the center of gravity G agree with the rotary shaft S, a user of the microscope 5 is only required to push the switch 20 once. Then, an automatic weight balancing action according to the present invention starts.

Horizontalizing

Figure 11:
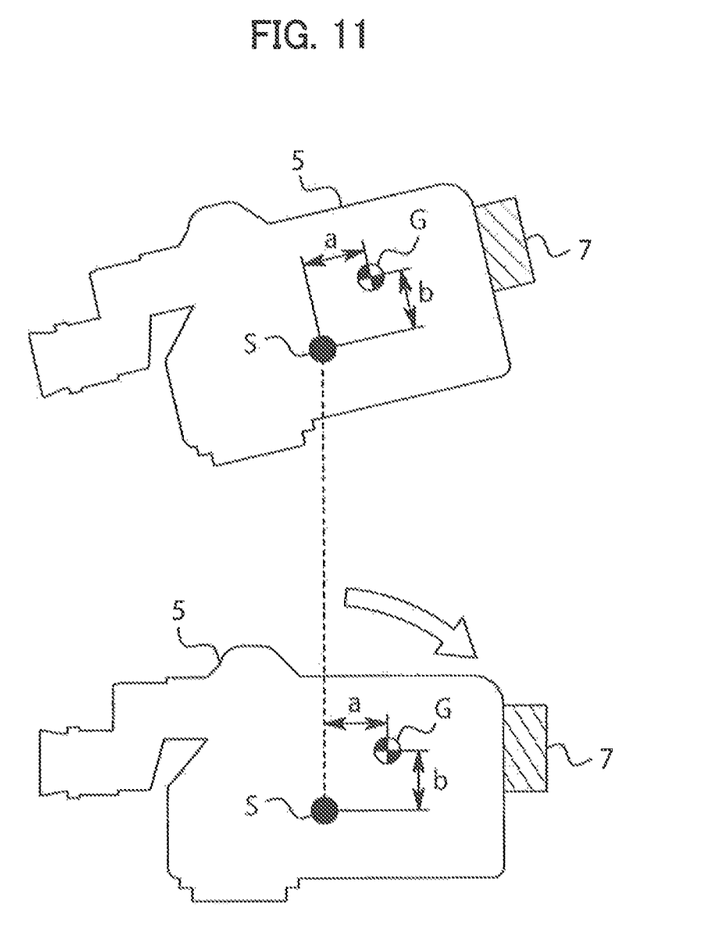
FIG. 11 is an explanatory view illustrating the surgical microscope turned to a horizontal state.

FIG. 11 shows the surgical microscope 5 and the co-observation unit 7 connected to the back of the surgical microscope 5. Due to the co-observation unit 7, the center of gravity G of the surgical microscope 5 is displaced by "a" in a lateral direction and by "b" in a longitudinal direction. In FIG. 11, the co-observation unit 7 is simplified. In an initial state, the surgical microscope 5 as a whole may not be horizontal but may slightly be inclined.

When the switch 20 is pushed, the horizontal sensor 17 starts to operate. If the horizontal sensor 17 detects that the surgical microscope 5 is not horizontal, the electric driving unit 16 turns the surgical microscope 5 together with the electric slide mechanism 8 into a horizontal state. When the surgical microscope 5 is brought into the horizontal state, the horizontal sensor 17 detects the same and stops the turning of the surgical microscope 5.

Balancing by Lateral Slider

Figure 12:
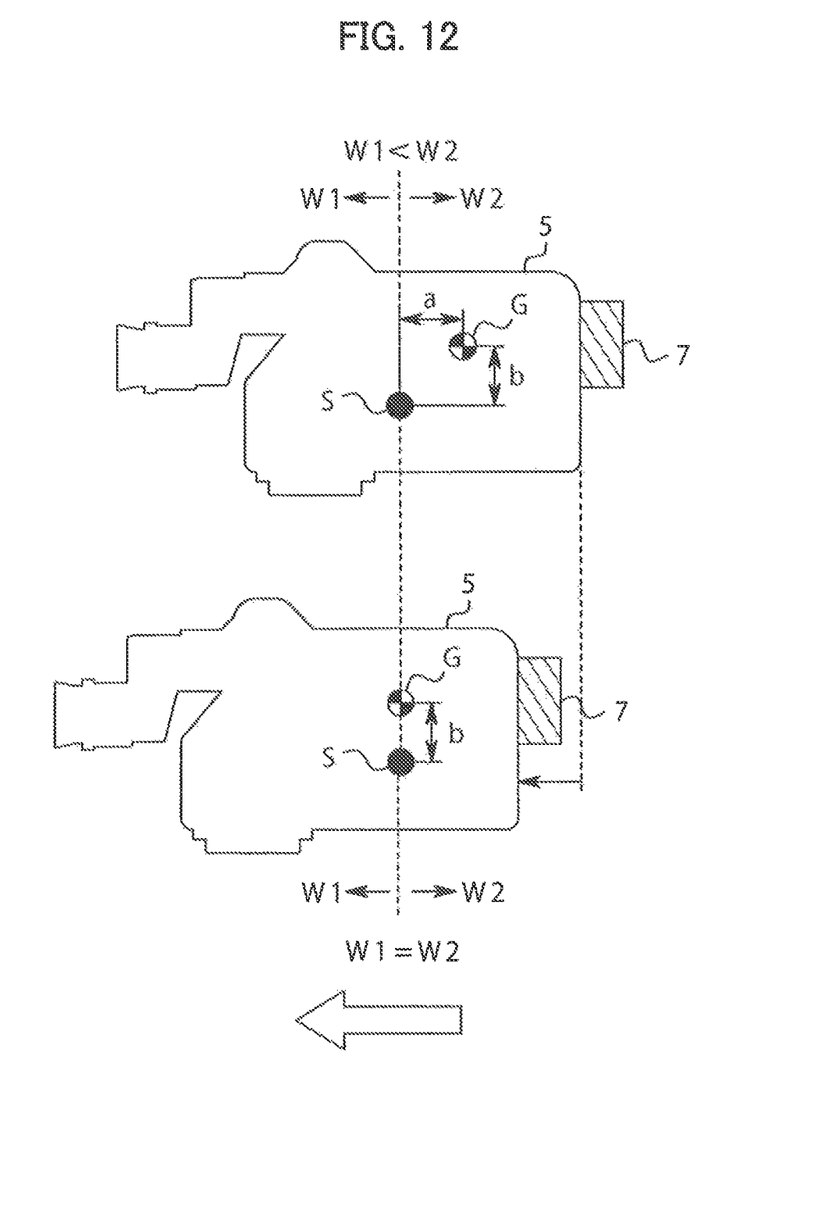
FIG. 12 is an explanatory view illustrating the horizontally set surgical microscope slid in the front-back direction.

After the surgical microscope 5 is set to the horizontal state, the rotary shaft S is released from the electric driving unit 16 so that the rotary shaft S may freely turn. Thereafter, the balance sensor 18 is activated to detect a weight balance of the surgical microscope 5 in the front-back direction around the rotary shaft S. If the weight balance in the front-back direction is imbalanced, the lateral slider 9 is driven to slide the surgical microscope 5 in a balancing direction. For example, in FIG. 12, the center of gravity G of the surgical microscope 5 is behind the rotary shaft S, and therefore, a rear weight W2 of the surgical microscope behind the rotary shaft S is greater than a front weight W1 thereof in front of the rotary shaft S. Accordingly, the lateral slider 9 is driven to move the surgical microscope 5 frontward to adjust the position of the center of gravity G to the position of the rotary shaft S in the front-back direction. As a result, the front-back position of the surgical microscope 5 is adjusted to the rotary shaft S. However, an up-down position of the surgical microscope 5 is not yet adjusted to the rotary shaft S.

45-Degree Turning and Balancing by Longitudinal Slider

Once the center of gravity G of the surgical microscope 5 is aligned with the rotary shaft S in the front-back direction, the electric driving unit 16 forwardly turns the surgical microscope 5 together with the electric slide mechanism 8 by 45 degrees.

The 45-degree turn slants the displacement of the center of gravity G relative to the rotary shaft S. At this time, the longitudinal slider 10 is also inclined by 45 degrees, and therefore, the direction of the displacement of the center of gravity G is kept in the direction of the longitudinal slider 10. Namely, the state in which the center of gravity G of the surgical microscope 5 is agreeing with the rotary shaft S in the front-back direction is kept as it is even after the surgical microscope 5 is turned together with the electric slide mechanism 8 to the oblique state.

Figure 13:
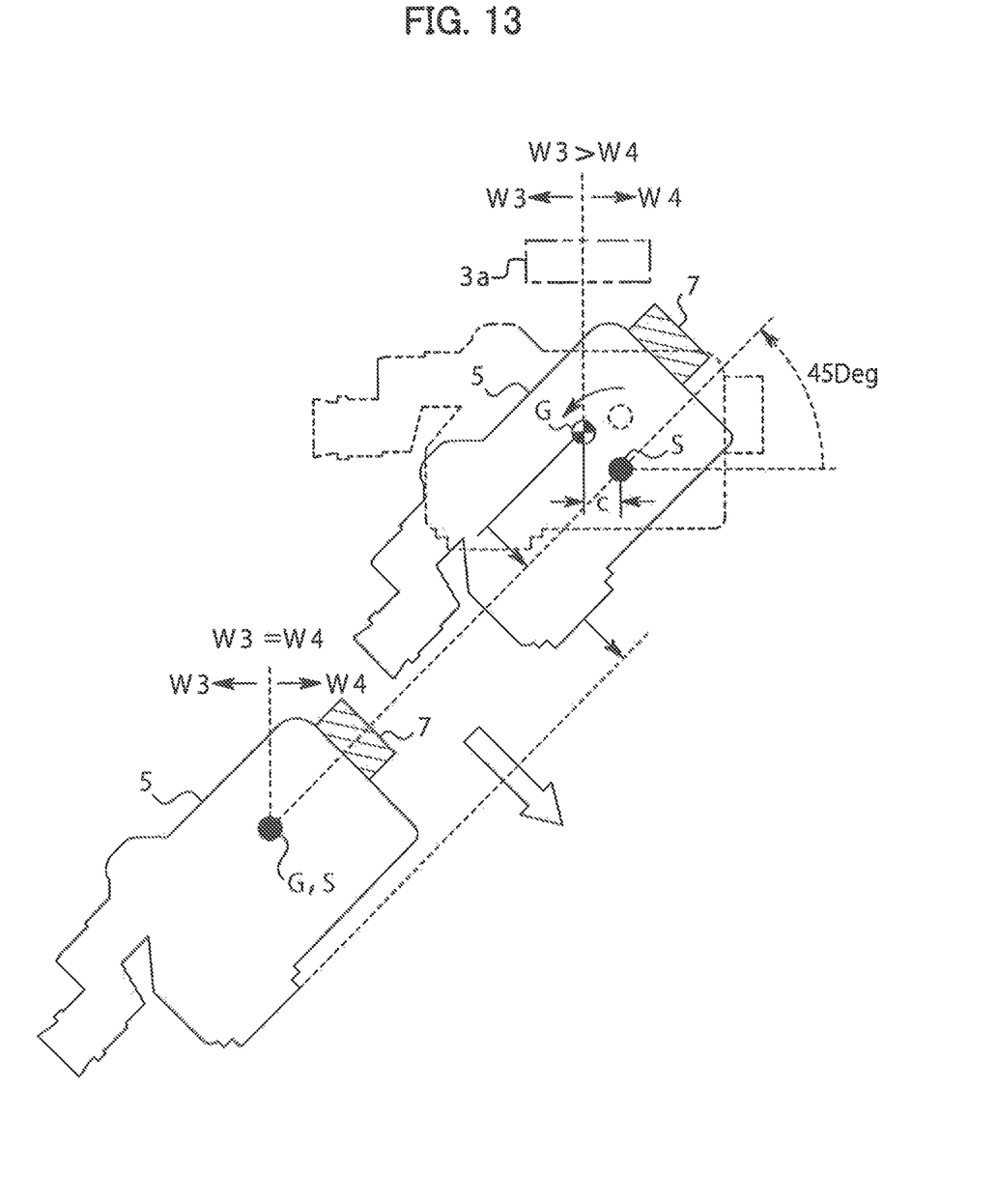
FIG. 13 is an explanatory view illustrating the surgical microscope set in an oblique state and slid along a longitudinal slider.

Since the displacement of the center of gravity G slants, the displacement of the center of gravity G involves a component "c" in the front-back direction as illustrated in FIG. 13. As a result, a front weight W3 of the surgical microscope 5 in front of the rotary shaft S is greater than a rear weight W4 behind the rotary shaft S.

The rotary shaft S is released to freely turn and the balance sensor 18 is activated. The balance sensor 18 detects the displacement "c" and the surgical microscope 5 is slid along the longitudinal slider 10 in a direction to correct the weight imbalance. Since the longitudinal slider 10 is at an angle of 45 degrees and agrees with the direction of the displacement of the center of gravity G, sliding the surgical microscope 5 along the longitudinal slider 10 negates the displacement "c" in the front-back direction so that the center of gravity G agrees with the rotary shaft S.

Once the center of gravity G agrees with the rotary shaft S, the rotary shaft S is able to be released to freely turn so that the surgical microscope 5 may manually be turned to an optional state without loosing the weight balance. Even if the hand is removed from the surgical microscope 5, the surgical microscope 5 will maintain the optional state. Only by pushing the switch 20 at the beginning, the center of gravity G of the surgical microscope 5 is automatically adjusted to the rotary shaft S. This operation is very easy to carry out.

As mentioned above, an offset of the center of gravity G from the rotary shaft S is a combination of the lateral displacement "a" and longitudinal displacement "b". After the lateral displacement "a" is balanced, the displacement component "c" reflects only the longitudinal displacement "b". Accordingly, even if the offset direction of the center of gravity G is not horizontal with respect to the rotary shaft S, the longitudinal displacement "b" is correctable.

According to the embodiment, the surgical microscope 5 is turned only by 45 degrees and this turning operation requires, even if automated, only a short time. Namely, the turning operation will complete within a short time. The 45-degree turn never makes the co-observation unit 7 attached to the back of the surgical microscope 5 protrude upward to interfere with the horizontal part 3*a* of the suspension arm 3.

Figure 1:
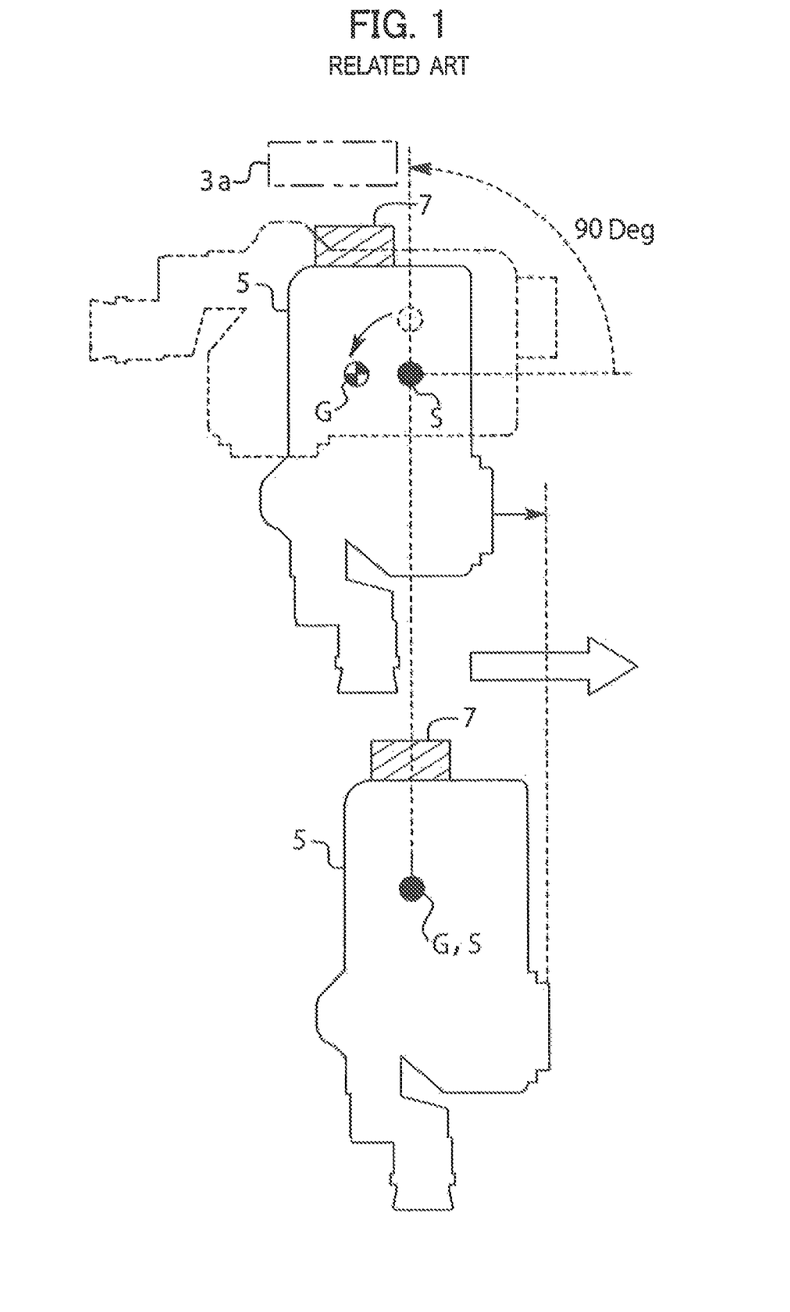
FIG. 1 is an explanatory view illustrating a related art that turns a surgical microscope by 90 degrees and slides the surgical microscope.

If the surgical microscope 5 must be turned by 90 degrees like the related art of FIG. 1, the electric driving unit 16 needs a longer time to complete the turning operation. In addition, the co-observation unit 7 attached to the back of the surgical microscope 5 is vertically oriented to probably interfere with the horizontal part 3*a* of the suspension arm 3.

Although the embodiment turns the surgical microscope 5 by 45 degrees, this turning angle does not limit the present invention. There is no specific turning angle according to the present invention. The turning angle, however, is preferably 30 degrees or greater in order to easily detect a displacement of the center of gravity G of the surgical microscope 5 in the front-back direction. Although the embodiment installs the lateral slider 9 on the surgical microscope 5 side and the longitudinal slider 10 on the rotary shaft S side, it is possible to install the lateral slider 9 on the rotary shaft S side and the longitudinal slider 10 on the surgical microscope 5 side.

In this way, the present invention requires only a switching operation to automatically align the center of gravity of a surgical microscope with a rotary shaft, thereby easily accomplishing a weight balance of the surgical microscope. Unlike the related art that must turn the surgical microscope by 90 degrees, the present invention only slants the surgical microscope. This slanting operation needs, even if automated, a shorter time than the 90-degree turn. Unlike the related art that turns the surgical microscope by 90 degrees, the present invention only obliquely turns the surgical microscope, and therefore, no part of the surgical microscope protrudes upward to interface with a part of a supporting structure of the surgical microscope.

What is claimed is:

1. An automatic weight balance mechanism for a surgical microscope having on its front side a left-right pair of eyepieces, the weight balance mechanism rotatably supporting a side face of the surgical microscope on an attaching part arranged at a front end of a support arm laterally extending from a stand apparatus so that the surgical microscope is configured to turn around a horizontal rotary shaft arranged at the attaching part and extending in a left-right direction, the weight balance mechanism comprising:

an electric slider interposed between the surgical microscope and the attaching part, to slide the surgical microscope relative to the rotary shaft in up-down and front-back directions of the surgical microscope;

an electric driver having a clutch and arranged at the attaching part, to turn the surgical microscope together with the electric slider around the rotary shaft, and if required, make the surgical microscope including the electric slider freely turn;

a horizontal sensor to detect a horizontal state of the surgical microscope and a balance sensor to detect a weight balance of the surgical microscope including the electric slider in the front-back direction around the rotary shaft; and a controller that operates in response to a switching operation and sensing signals from the horizontal sensor and balance sensor, to turn the surgical microscope together with the electric slider around the rotary shaft and slide the surgical microscope by the electric slider relative to the rotary shaft so that a center of gravity of the surgical microscope is aligned with the rotary shaft, wherein the controller:

in response to the switching operation and horizontal sensor, drives the electric driver to turn the surgical microscope together with the electric slider around the rotary shaft until the surgical microscope is set to a horizontal state;

once the surgical microscope is set to the horizontal state, makes the rotary shaft freely turn and detects according to the balance sensor a front-back weight balance of the surgical microscope including the electric slider;

in a case where the front-back weight balance is imbalanced, drives the electric slider to slide the surgical microscope in a balancing direction;

in a case where the front-back weight balance is balanced, drives the electric driver to turn the surgical microscope together with the electric slider around the rotary shaft to an oblique state;

once the surgical microscope is set to the oblique state, makes the rotary shaft freely turn and detects according to the balance sensor a front-back weight balance of the surgical microscope including the electric slider; and in a case where the front-back weight balance is imbalanced, drives the electric slider to slide the surgical microscope in a balancing direction along an oblique direction so that the center of gravity of the surgical microscope including the electric slider agrees aligned with the rotary shaft.

2. The automatic weight balance mechanism of claim 1, wherein the oblique state of the surgical microscope has an angle of 30 degrees or greater with respect to the horizontal state.

3. The automatic weight balance mechanism of claim 1, wherein:

the electric slider includes a lateral slider extending along the front-back direction of the surgical microscope and a longitudinal slider orthogonal to the lateral slider; and one of the lateral and longitudinal sliders is fixed to the surgical microscope, the other is attached to the attaching part so as to be rotatable around the rotary shaft, the lateral slider is movable along the longitudinal slider, and the longitudinal slider is movable along the lateral slider.

* * * * *

UNITED STATES PATENT AND TRADEMARK OFFICE
CERTIFICATE OF CORRECTION

PATENT NO. : 10,830,979 B2
APPLICATION NO. : 16/002311
DATED : November 10, 2020
INVENTOR(S) : M. Ishima Page 1 of 1

It is certified that error appears in the above-identified patent and that said Letters Patent is hereby corrected as shown below:

In the Claims

At Column 7, Line 16 (Claim 1, Line 56), please change "slider agrees aligned" to -- slider aligned --.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*